(12) United States Patent
Merz et al.

(10) Patent No.: US 9,020,607 B2
(45) Date of Patent: Apr. 28, 2015

(54) IMPLANTABLE MULTI-ELECTRODE DEVICE

(71) Applicant: Sapiens Steering Brain Stimulation B.V., Eindhoven (NL)

(72) Inventors: Matthias Merz, Leuven (BE); Youri V. Ponomarev, Leuven (BE); Remco H.W. Pijnenburg, Hoogleoon (NL)

(73) Assignee: Sapiens Steering Brain Stimulation B.V., Eindhoven (NL)

( * ) Notice: Subject to any disclaimer, the term of this patent is extended or adjusted under 35 U.S.C. 154(b) by 0 days.

(21) Appl. No.: 14/315,869

(22) Filed: Jun. 26, 2014

(65) Prior Publication Data

US 2014/0309548 A1 Oct. 16, 2014

Related U.S. Application Data

(63) Continuation of application No. 12/442,133, filed as application No. PCT/IB2007/053775 on Sep. 18, 2007, now Pat. No. 8,798,737.

(60) Provisional application No. 60/826,608, filed on Sep. 22, 2006.

(51) Int. Cl.
*A61N 1/00* (2006.01)
*A61N 1/05* (2006.01)
*A61N 1/36* (2006.01)
(Continued)

(52) U.S. Cl.
CPC ............ *A61N 1/0529* (2013.01); *A61N 1/0531* (2013.01); *A61N 1/0534* (2013.01); *A61N 1/0536* (2013.01); *A61N 1/0539* (2013.01); *A61N 1/0558* (2013.01);
(Continued)

(58) Field of Classification Search
USPC .............. 607/45, 48, 116, 120, 128–130, 108
See application file for complete search history.

(56) References Cited

U.S. PATENT DOCUMENTS

| 3,943,936 A | 3/1976 | Rasor et al. |
| 5,593,431 A | 1/1997 | Sheldon |

(Continued)

FOREIGN PATENT DOCUMENTS

| EP | 1057496 A2 | 12/2000 |
| WO | 2004030706 A2 | 4/2004 |

(Continued)

OTHER PUBLICATIONS

Huai-Yuan Chu et al "Development of the Three Dimensional Multi-Electrode Array for Neural Recording" Solid State Sensors, Actuators and Microsystems, 2005, vol. 2, pp. 1804-1807.

(Continued)

*Primary Examiner* — Michael Kahelin
*Assistant Examiner* — Mallika D Fairchild
(74) *Attorney, Agent, or Firm* — Shumaker & Sieffert, P.A.

(57) ABSTRACT

The invention provides an implantable multi-electrode device (300) and related methods and apparatuses. In one embodiment, the invention includes an implantable device (300) comprising: an assembly block (320); and a plurality of leads (340 . . . 348) radiating from the assembly block (320), each of the plurality of leads (340 . . . 348) containing at least one electrode (342A), such that the electrodes are distributed within a three-dimensional space, wherein the assembly block (320) includes a barb (350) for anchoring the assembly block (320) within implanted tissue.

14 Claims, 7 Drawing Sheets (51) Int. Cl.
*A61B 5/04* (2006.01)
*A61L 31/14* (2006.01)

(52) U.S. Cl.
CPC ....... *A61N 1/36082* (2013.01); *A61B 5/04001* (2013.01); *A61L 31/148* (2013.01)

(56) References Cited

U.S. PATENT DOCUMENTS

| | | | |
|---|---|---|---|
| 5,653,742 | A | 8/1997 | Parker et al. |
| 6,091,979 | A | 7/2000 | Madsen |
| 6,582,441 | B1 | 6/2003 | He et al. |
| 8,010,208 | B2 | 8/2011 | Nimer et al. |
| 2003/0139782 | A1 | 7/2003 | Duncan et al. |
| 2003/0233126 | A1 | 12/2003 | Kaplan et al. |
| 2004/0015211 | A1 | 1/2004 | Nurmikko |
| 2004/0199235 | A1* | 10/2004 | Younis ............ 607/116 |
| 2005/0203366 | A1 | 9/2005 | Donoghue |
| 2006/0032657 | A1 | 2/2006 | Zarembo |
| 2007/0088417 | A1* | 4/2007 | Schouenborg ........ 607/116 |

FOREIGN PATENT DOCUMENTS

| WO | 2006069322 | A2 | 6/2006 |
|---|---|---|---|
| WO | 2007010441 | A2 | 1/2007 |

OTHER PUBLICATIONS

Heuschkel M.O. et al "A Three-Dimensional Multi-Electrode Array for Multi-Site Stimulation and Recording in Acute Brain Slices" Journal of Neuroscience Methods, vol. 114, Jan. 2002, pp. 135-148.

\* cited by examiner

Figure 2:
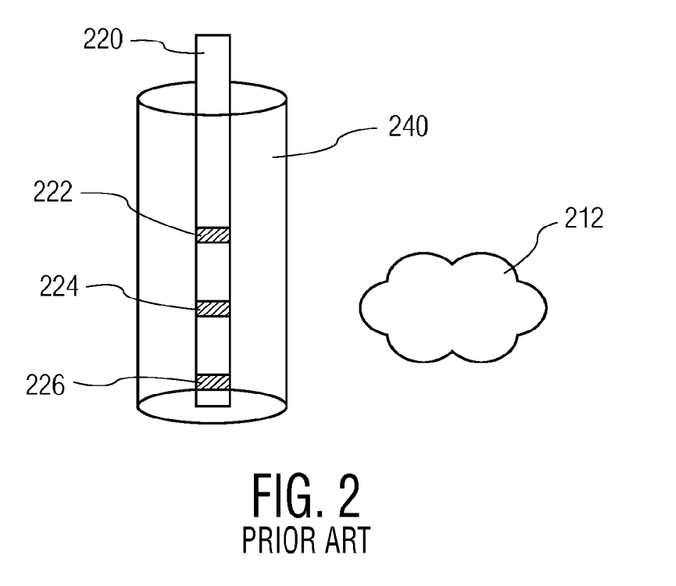
FIG. 2 shows a detailed view of the device of FIG. 1.

FIG. 8E ical volume immediately surrounding the electrode. FIG. 2 shows a simplified view of a known lead 220 housing three electrodes 222, 224, 226. Together, electrodes 222, 224, and 226 are capable of stimulating a volume 240 of the brain adjacent lead 220. As can be seen in FIG. 2, volume 240 is substantially cylindrical. In the case that a targeted area 212 of the brain lies outside volume 240, it is very difficult or impossible to stimulate the targeted area 212 using known electrodes such as that shown in FIG. 2. Increasing the amplitude of the electrical signal applied to the electrodes will increase volume 240, but is still unlikely to reach the targeted area 212 unless the targeted area 212 is very near lead 220. In addition, the extent to which the amplitude of the electrical signal may be increased is limited by the onset of tissue damage adjacent lead 220.

IMPLANTABLE MULTI-ELECTRODE DEVICE

CROSS-REFERENCE TO RELATED APPLICATIONS

This application is a continuation of pending U.S. patent application Ser. No. 12/442,133 filed on Sep. 18, 2007, which is a U.S. National Stage of International Patent Application No. PCT/IB2007/053775 filed on Sep. 18, 2007, which claims priority to U.S. Provisional Patent Application No. 60/826,608 filed on Sep. 22, 2006, all of which are incorporated herein by reference in their entirety.

The invention relates generally to electrode devices, and more particularly, to an implantable, multi-electrode device, as well as devices for its encapsulation and implantation.

Many neurological diseases and conditions include tremors among their symptoms. Often, such tremors are only partially treatable with medication. In other cases, the effect of the medication decreases as the disease or condition progresses. In some cases, such as severe Parkinson's Disease, medicinal treatment is ineffective in controlling such tremors.

One treatment currently available to patients suffering from drug-resistant tremors is brain surgery in which lesions are formed in areas of the brain believed to be responsible for the tremors. However, while such surgery has been shown to provide some relief of tremor symptoms, the irreversibility of such treatment presents a major drawback. For example, if it is determined that the surgery failed to alleviate tremor symptoms and/or resulted in an undesired impairment of normal brain activity, a patient is left without remedy.

Figure 1:
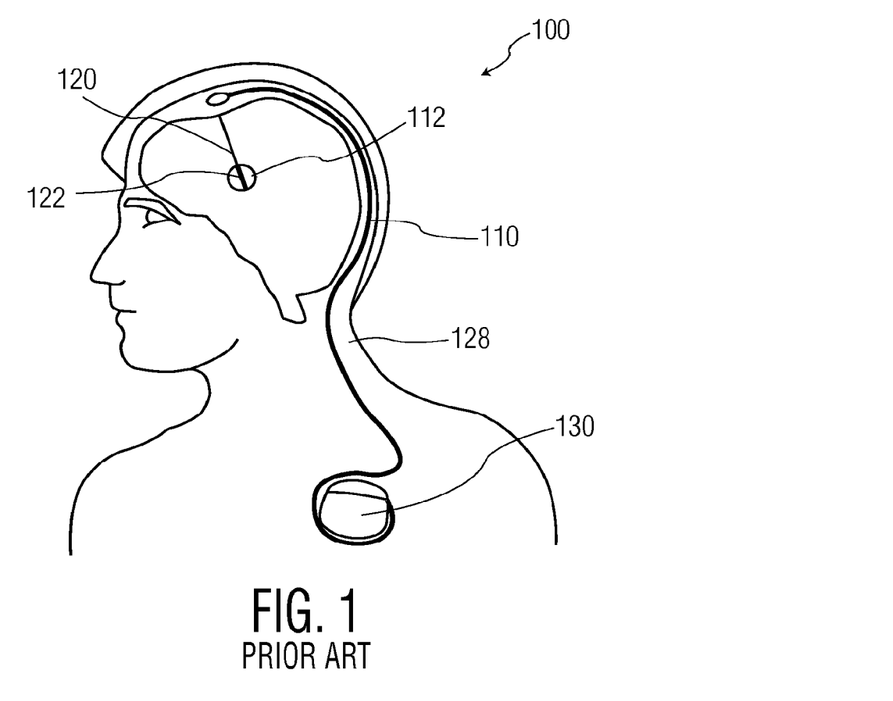
FIG. 1 shows a known deep brain stimulation (DBS) device.

An alternative treatment for drug-resistant tremors involves the electrical stimulation of areas of the brain responsible for tremor symptoms. These areas include the subthalamic nucleus (STN), the globus pallidus interna (GPi), and the ventral intermediate nucleus (VIM) of the thalamus. For example, referring to FIG. 1, the targeted areas 112 of the brain 110 of an individual 100 are electrically stimulated via one or more electrodes 122 carried by a lead 120 surgically implanted in the brain 110. Accordingly, such treatment is commonly referred to as deep brain stimulation (DBS). Electrical pulses are typically supplied to the implanted electrode 122 using a pacemaker-like neurostimulator 130 implanted in the individual's chest, which are connected by a signal wire 128 beneath the individual's skin.

While DBS is generally reversible (i.e., electrodes may be surgically removed and/or relocated), the electrodes currently in use provide little variability in the volume of the brain around the electrode that is stimulated. That is, the volume stimulated by known electrodes comprises a generally cylin- To this extent, a need exists for methods and devices for treating individuals suffering from tremor symptoms that do not suffer from the defects known in the art.

The invention provides an implantable multi-electrode device and related methods and apparatuses. In one embodiment, the invention includes an implantable device comprising: an assembly block; and a plurality of leads radiating from the assembly block, each of the plurality of leads containing at least one electrode, such that the electrodes are distributed within a three-dimensional space, wherein the assembly block includes a barb for anchoring the assembly block within implanted tissue.

A first aspect of the invention provides a method for delivering an electrical stimulus to nervous tissue of an individual, the method comprising: implanting in the nervous tissue of an individual a stimulatory device including: an assembly block; and a plurality of leads extending from the assembly block, each of the plurality of leads containing at least one electrode, such that the electrodes become distributed within a targeted volume of the nervous tissue; and administering to the nervous tissue an electrical stimulus using at least one electrode.

A second aspect of the invention provides an implantable device comprising: an assembly block; and a plurality of leads radiating from the assembly block, each of the plurality of leads containing at least one electrode, such that the electrodes are distributed within a three-dimensional space.

A third aspect of the invention provides a system for implanting an implantable device, the system comprising: implantable device including: an assembly block; and a plurality of leads radiating from the assembly block, each of the plurality of leads containing at least one electrode, such that the electrodes are distributed within a three-dimensional space; and an apparatus for implanting the implantable device comprising: an outer tube; an inner tube; and a mating feature on a surface of the inner tube compatible with a feature on a surface of an implantable device, wherein an inner diameter of the outer tube is at least as great as an outer diameter of the inner tube, such that the implantable device may be moved through the outer tube by the inner tube.

A fourth aspect of the invention provides an apparatus for implanting an implantable device comprising: an outer tube; an inner tube; and a mating feature on a surface of the inner tube compatible with a feature on a surface of an implantable device, wherein an inner diameter of the outer tube is at least as great as an outer diameter of the inner tube, such that the implantable device may be moved through the outer tube by the inner tube.

A fifth aspect of the invention provides a method for protecting an implantable device, the method comprising: applying an encapsulant to a surface of at least a portion of an implantable device.

The illustrative aspects of the present invention are designed to solve the problems herein described and other problems not discussed, which are discoverable by one skilled in the art.

These and other features of this invention will be more readily understood from the following detailed description of the various aspects of the invention taken in conjunction with the accompanying drawings that depict various embodiments of the invention, in which:

It is noted that the drawings of the invention are not to scale. The drawings are intended to depict only typical aspects of the invention, and therefore should not be considered as limiting the scope of the invention. In the drawings, like numbering represents like elements between the drawings.

Figure 3A:
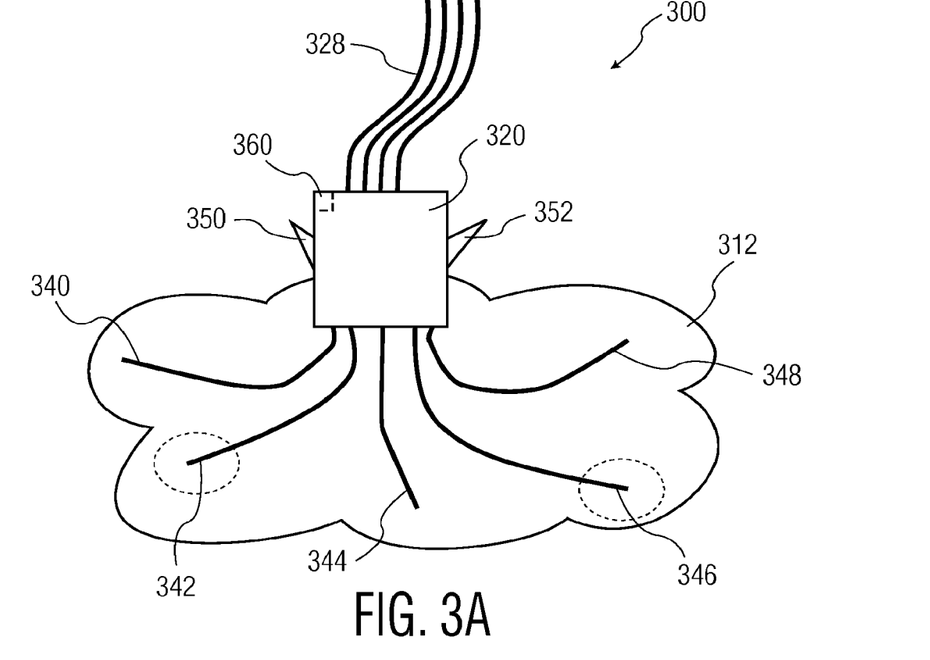
FIG. 3A shows an illustrative device according to the invention.
Figure 3B:
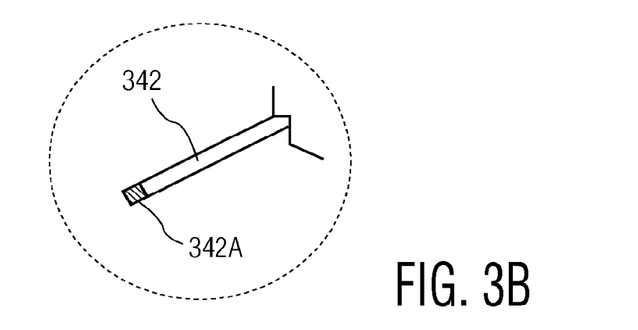
FIGS. 3B-C show detailed views of portions of the device of FIG. 3A.
Figure 3C:
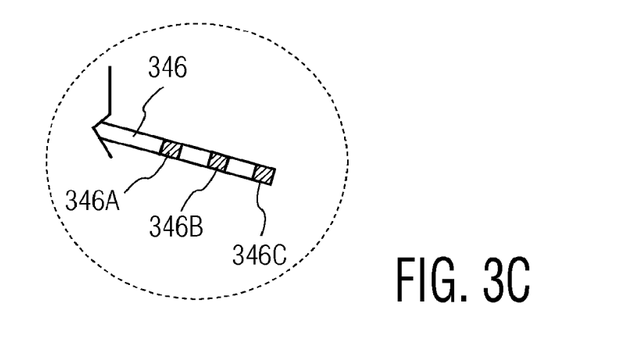

As indicated above, the invention provides an implantable, multi-electrode device. FIGS. 3A-C show general and detailed views of an illustrative device according to the invention. In FIG. 3A, device 300 comprises an assembly block 320 from which extend one or more lead wires 328 and a plurality of flexible leads 340, 342, 344, 346, 348, the plurality of leads being distributed in a three-dimensional space. Leads 340, 342, 344, 346, 348 may have a smaller diameter than known electrode devices (see, e.g., FIGS. 1-2). Preferably, each lead 340, 342, 344, 346, 348 has a diameter less than about 2 mm and a length less than about 40 mm and is stiff enough to penetrate into brain tissue during implantation.

Assembly block 320 may have any number of forms, that depicted in FIG. 3A being merely illustrative. For example, assembly block 320 may comprise a tube through which the plurality of leads passes. Alternatively, in one preferred embodiment, assembly block 320 includes electronic multiplexing circuitry operable to distribute a stimulus from lead wires 328 to one or more of leads 340 . . . 348. In such an embodiment, the number of lead wires 328 may be reduced, as they need to supply only the assembly block 320 rather than each of the plurality of leads 340 . . . 348. This provides a number of advantages, including easier implantation due to lead wires being smaller and/or more flexible, and decreased mechanical forces transferred from the skull to device 300. In such an embodiment, the electronic multiplexing circuitry may be controlled using, for example, an additional lead wire or a radio frequency telemetry link.

By using a plurality of smaller leads in a more "fanned out" three-dimensional distribution, a volume of targeted area 312 may be more precisely matched than is possible using known devices. That is, while the plurality of smaller leads of the present invention are capable of delivering approximately the same maximum power as known single-lead devices, the more precise placement of the plurality of leads permits the use of less power. In addition, each lead may include one or more electrodes. For example, as shown in FIG. 3B, lead 342 includes a single electrode 342A adjacent its distal end. Contrarily, FIG. 3C shows a detailed view of lead 346, which includes three electrodes 346A-C distributed along its length. While thus far described as delivering a stimulatory signal, it should be recognized that one or more electrode(s) may alternatively be used to measure and/or record a level of neurostimulation in an area where the electrode(s) is/are implanted.

As noted above, because some electrodes of the present invention are closer to the target area, the stimulation amplitude (for achieving the same clinical effects) is smaller than for known electrode devices. This provides a number of advantages. First, the use of a stimulatory signal having a lower amplitude reduces the risk of tissue damage adjacent the electrodes. Second, the combination of a lower amplitude signal and a more accurate placement of each electrode reduces side effects resulting from stimulation of non-targeted areas of the brain. Third, the use of lower amplitude stimulation extends the life of battery-powered pulse generators (e.g., pacemaker-like neurostimulator 130 in FIG. 1).

Device 300 may be supplied with leads prearranged by length, number, and orientation to match a known target area (e.g., the subthalamic nucleus (STN), the globus pallidus interna (GPi), and the ventral intermediate nucleus (VIM) of the thalamus). Alternatively, the arrangement of the leads may be customized according to a target area determined using an imaging device (e.g., a magnetic resonance imaging (MRI) device, a computerized tomography (CT) device, etc.). Similarly, if it is determined after implantation that only a portion of the targeted area 312 needs to be stimulated (e.g., is responsible for a tremor symptom), the electrode(s) of only a subset of leads 340, 342, 344, 346, 348 may be activated. This may be achieved using, for example, an assembly block containing electronic multiplexing circuitry, as explained above.

While electrical stimulation of a targeted area of the brain may itself be sufficient to reduce or prevent tremor symptoms in an individual, it may, in some cases, be desirable to also administer to the individual one or more anti-tremor medications. In such a case, the dosage of anti-tremor medication(s) is preferably lower than would be pharmaceutically effective without concurrent electrical stimulation of a targeted area of the brain.

As shown in FIG. 3A, assembly block 320 may optionally include one or more barbs 350, 352 for anchoring assembly block 320 within the individual's brain tissue. In one embodiment, the one or more barbs may be adapted to fold against or be contained within assembly block 320 during implantation and, once device 300 is in place, protrude from assembly block 320. In another embodiment, the one or more barbs 350, 352 may be retractable, such that removal of an implanted device 300 may be eased. Assembly block 320 preferably includes a notch 360 or similar feature for controlling and/or monitoring (i.e. determining) the angular orientation and/or rotation of device 300 during implantation. Preferably, assembly block 320 has a maximum diameter of less than 5 mm.

Preferably, lead wires 328 are contained within a flexible, insulated wire assembly in order to minimize the transmission of force from the skull (to which lead wires 328 will ultimately be attached) to the brain tissue. This allows device 300 to move freely.

While thus far described as useful in the treatment of diseases or disorders exhibiting tremor symptoms, such as Parkinson's Disease, it should be recognized that electrical stimulation of targeted areas of the brain is known to be effective in the treatment of other diseases and disorders. Accordingly, devices and methods of the present invention are applicable to the treatment of any disease or disorder now known or later found to be treatable using electrical stimulation of a targeted area of the brain. Currently, these include, for example, depression, bipolar disorders, obsessive convulsive disorder, and epilepsy.

As will be recognized by one having skill in the art, the act of implanting any device into the brain tissue of an individual is likely to cause some damage to the affected tissue. As a consequence, the individual's immune system will typically mount a response to such damage. Specifically, an acute inflammatory response is often noted in areas suffering damage. Once the acute inflammatory response has subsided, an encapsulating tissue layer is frequently formed around the implanted device. This can have a particularly negative effect on the function of the device, as the encapsulating tissue layer obstructs, hampers, or otherwise interferes with electrical coupling between the device and the surrounding nervous (e.g., brain) tissue.

Similarly, the device may become contaminated by dead cells and/or tissue during the implantation procedure itself. This is more likely where the surface of the device is coated with adhesion molecules (e.g., polylysine, laminine, fibronectine, etc.) for promoting the adhesion of nervous tissue to the device. These materials are very sticky and likely to bind to unintended materials during implantation, thus reducing the function of the device.

In addition, the device itself may be damaged during the implantation procedure, by contact with either the implantation tools or the nervous tissue. The latter is more likely where the device includes delicate topographic structures, such as pillars, which are helpful in promoting contact between electrodes of the device and neurons. Topographic structures or any "rough" surface of the device may also lead to increased tissue damage during implantation.

Figure 4:
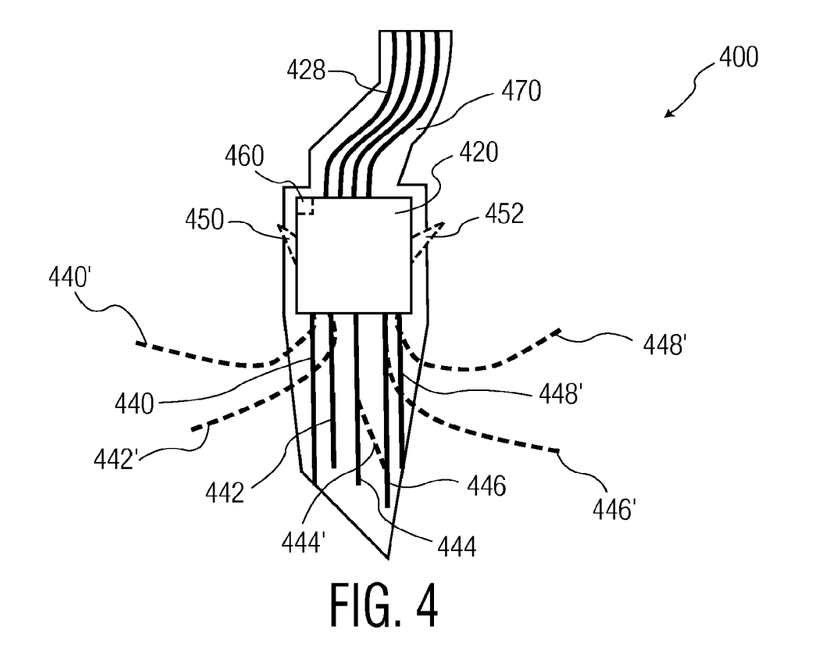
FIG. 4 shows an illustrative encapsulated device according to the invention.

Accordingly, it may be desirable to coat implanted devices with a biodegradable protective material prior to implantation. FIG. 4 shows an encapsulated device 400 similar to device 300 of FIG. 3A. As can be seen in FIG. 4, the entirety of device 400 is covered by a biodegradable encapsulant 470. Materials suitable for use in encapsulant 470 include, for example, polylactic acid (PLA), polyglycolic acid (PGA), polydioxanone (PDS), polyethylene glycol (PEG), and polyhydroxy butyrate (PHB). Other suitable materials will, of course, be recognized by one skilled in the art.

Encapsulant 470 may be applied using any known or later-developed method or technique. Preferred methods include injection moulding, spraying, and vapor deposition. The particular method chosen will depend, of course, on a number of factors, including the device to be encapsulated, the composition of the encapsulant, and the desired thickness of the finished encapsulant.

Encapsulant 470 provides a number of advantages over a non-encapsulated device, including protection of the encapsulated device from mechanical damage during implantation, protection of the encapsulated device from contamination with dead cells and/or tissue, protection of adhesion molecules, eased implantation due to a smoother surface, and reduced inflammatory response. Inflammatory response may be further reduced by incorporating into the encapsulant itself one or more anti-inflammatory compound. In such an embodiment, the anti-inflammatory compound(s) is/are released into the tissue surrounding the implanted device as the encapsulant biodegrades. To further increase the adhesion and coupling between neuronal tissue and electrode growth promoting proteins (trophic factors) may also be added to the encapsulant.

As shown in FIG. 4, leads 440 . . . 448, when contained within encapsulant 470, may have a substantially "unfanned" distribution and, once encapsulant 470 has sufficiently degraded, adopt the "fanned" distribution of leads 440' . . . 448' (shown in phantom).

As will be described in greater detail below, encapsulant 470 may optionally be formed into a sharp or pointed leading edge such that encapsulant 470 itself may be used to cut through tissue during the implantation procedure and aid in the passage of device 400 to its intended implantation site.

Figure 5A:
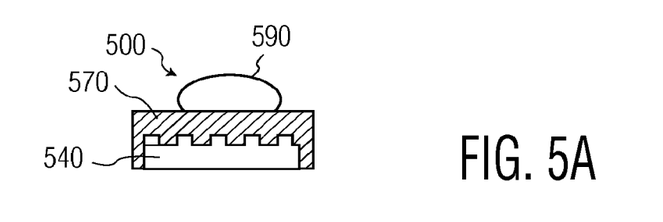
FIGS. 5A-C show sequential steps in the degradation of an encapsulant according to the invention.
Figure 5B:
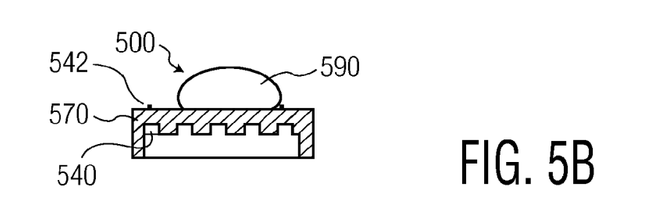
Figure 5C:
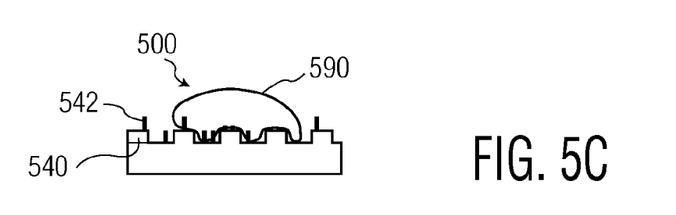

FIGS. 5A-C show the gradual degradation of encapsulant 570 from an implantable device 500 having topographic structures 540, 542. In FIG. 5A, device 500 is fully encapsulated and an adjacent neural cell (e.g., neuron) 590 contacts encapsulant 570. In FIG. 5B, a portion of encapsulant 570 has degraded such that neuron 590 may contact the uppermost topographic structure 542. In FIG. 5C, encapsulant 570 is completely degraded and neuron 590 is free to contact any portion of device 500, including topographic structure 540.

While the encapsulant of the present invention has been described as useful in encapsulating a multi-electrode device for implantation in brain tissue, it should be recognized that the encapsulants described herein may similarly be applied to any implantable device. Encapsulants of the present invention are particularly useful in encapsulating devices requiring a good electrical contact with surrounding tissue. Such devices include, for example, retinal implants, deep brain stimulation (DBS) electrodes, recording electrodes used in the motor cortex e.g. to control a prosthesis, and devices for stimulating neural activity (e.g., for stimulating the somatosensory cortex or delivering input from another device, such as a camera). Such devices are described in U.S. Provisional Patent Application No. 60/701,337, filed 21 Jul. 2005 and International Patent Application No. PCT/US2006/052348, filed 11 Jul. 2006, each of which is incorporated herein by reference.

Figure 6A:
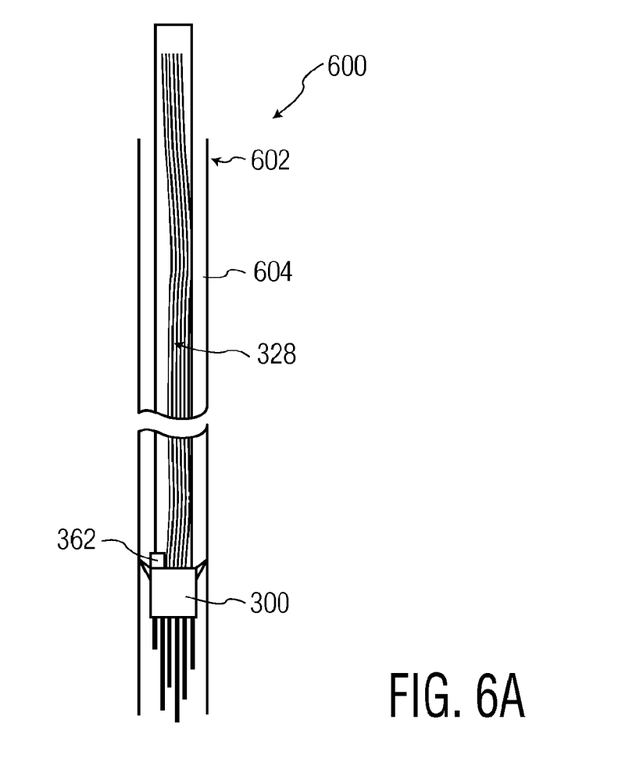
FIGS. 6A-C show general and detailed views of a device and implantation apparatus according to the invention.
Figure 6B:
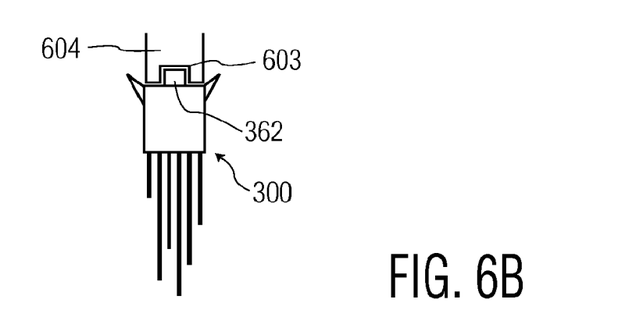
Figure 6C:
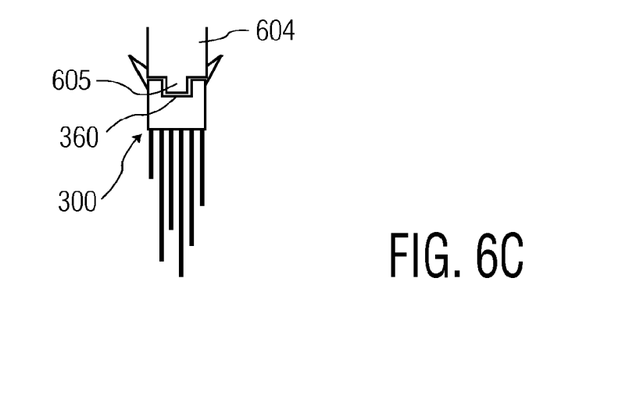

As noted above, devices according to the invention may optionally include a notch or similar feature for controlling and/or monitoring (i.e. determining) the angular orientation and/or rotation of the device during implantation. FIGS. 6A-C show alternative embodiments of a device 300 in association with an implantation apparatus 600 according to the invention. As shown, implantation apparatus 600 comprises an outer tube 602 and an inner tube 604, the inner tube 604 having an outer diameter less than or equal to an inner diameter of the outer tube 602, such that inner tube 604 may slide within outer tube 602. As shown in FIG. 6A, and in greater detail in FIG. 6B, device 300 includes a ridge 362 compatible with a mating feature 603 of inner tube 604, such that device 300 may be moved through outer tube 602 as inner tube 604 passes within outer tube 602. Preferably, at least one of the angular orientation and the rotation of device 300 may be determined and/or controlled using ridge 362 and mating feature 603, as will be recognized by one skilled in the art. As can be seen in FIG. 6A, and will be described in greater detail below, lead wires 328 may be extended through the interior space of inner tube 604.

FIG. 6C shows an alternative embodiment of the invention, wherein device 300 includes a notch 360 rather than a ridge, as in FIGS. 6A-B. Accordingly, mating feature 605 of inner tube 604 comprises a ridge rather than a grove, as in FIGS. 6A-B. Other shapes and combinations of features on device 300 and inner tube 604 may also be used, as will be recognized by one skilled in the art.

Figure 7A:
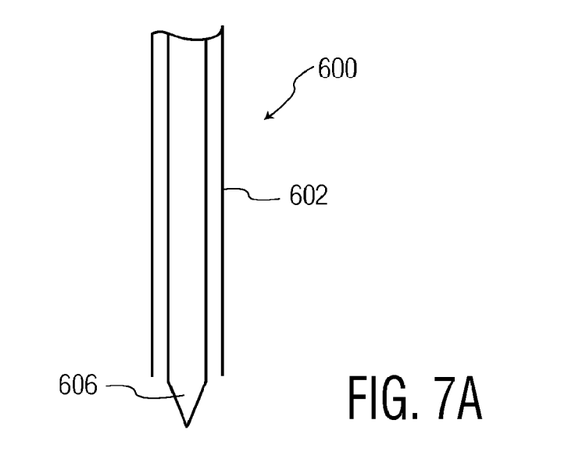
FIGS. 7A-C show alternative embodiments of implantation apparatuses and devices according to the invention.
Figure 7B:
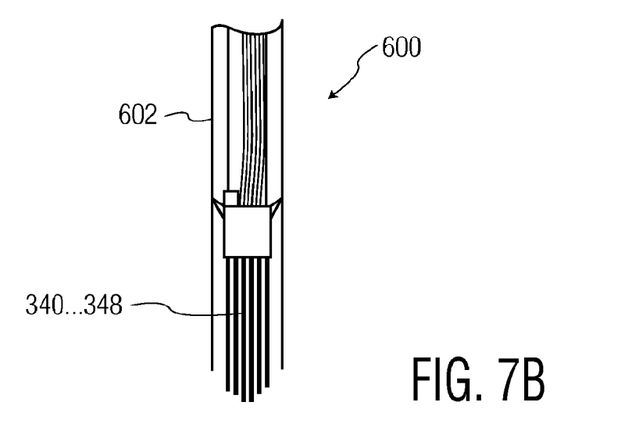
Figure 7C:
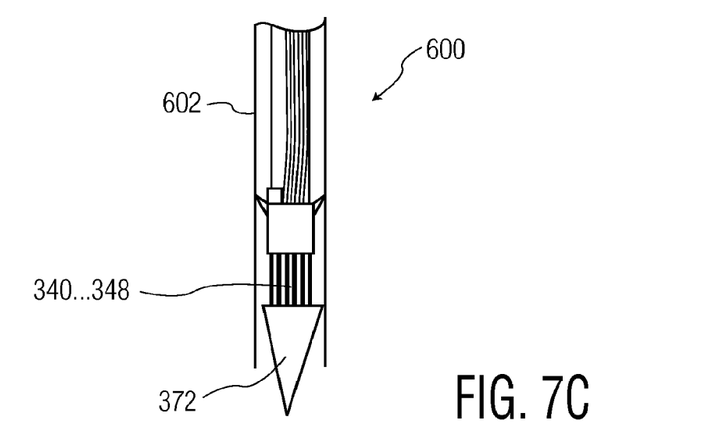

As noted above, it is possible that a device according to the invention may become contaminated with dead cells or tissue during implantation. Similarly, it is possible that the inner space of outer tube 602 may become blocked by cells or tissue during implantation of device 300. Accordingly, FIGS. 7A-C show illustrative embodiments of arrangements of implantation apparatus 600 capable of avoiding such blockage. In FIG. 7A, a sharp metal shaft 606 is provided within an end of outer tube 602, effectively closing or minimizing an available opening in outer tube 602. In addition, sharp metal shaft 606 may be used to pierce any tissue necessary during implantation of device 300. In FIG. 7B, individual leads 340 . . . 348 are arranged such that any opening in outer tube 602 is minimized. In FIG. 7C, a portion of encapsulant, as described above, has been formed into a sharp edge 372 at the tips of leads 340 . . . 348. As with sharp metal shaft 606, in addition to closing or minimizing an opening in outer tube 602, sharp edge 372 may be used to pierce any tissue necessary during implantation of device 300.

Figure 8A:
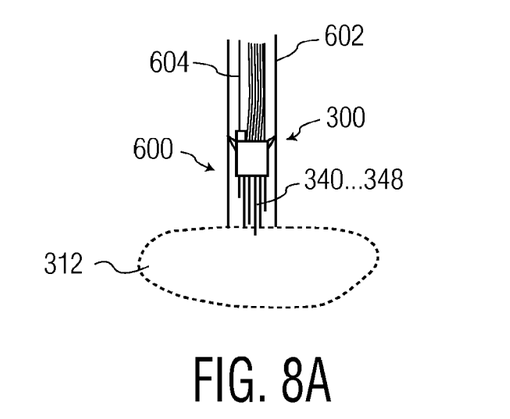
FIGS. 8A-E show sequential steps in the implantation of a device according to the invention using an implantation apparatus according to the invention.
Figure 8B:
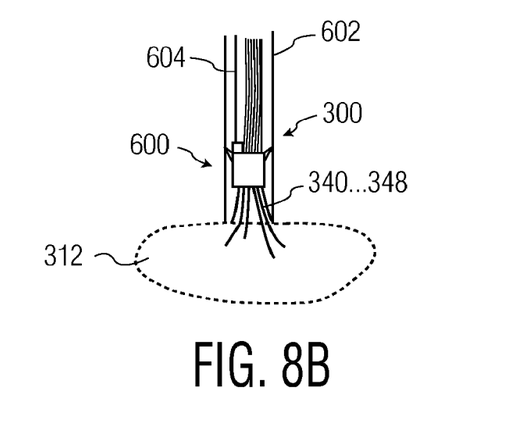
Figure 8C:
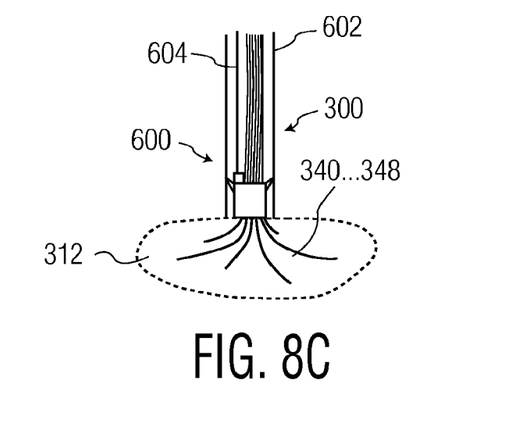
Figure 8D:
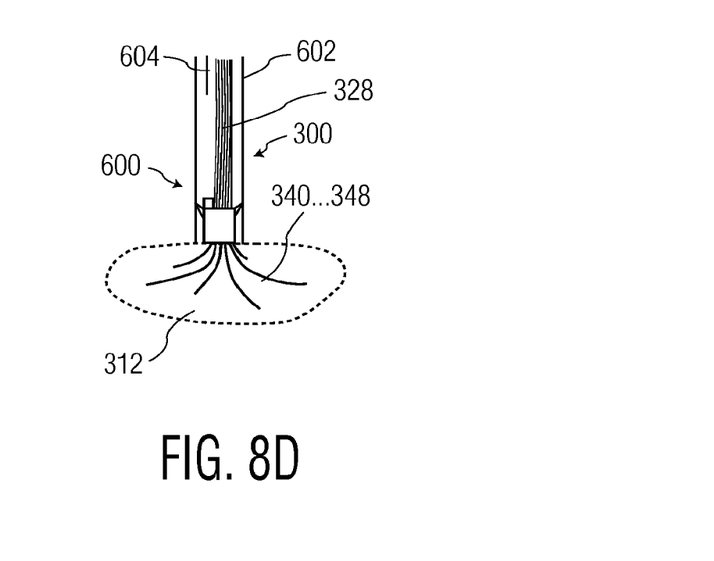
Figure 8E:
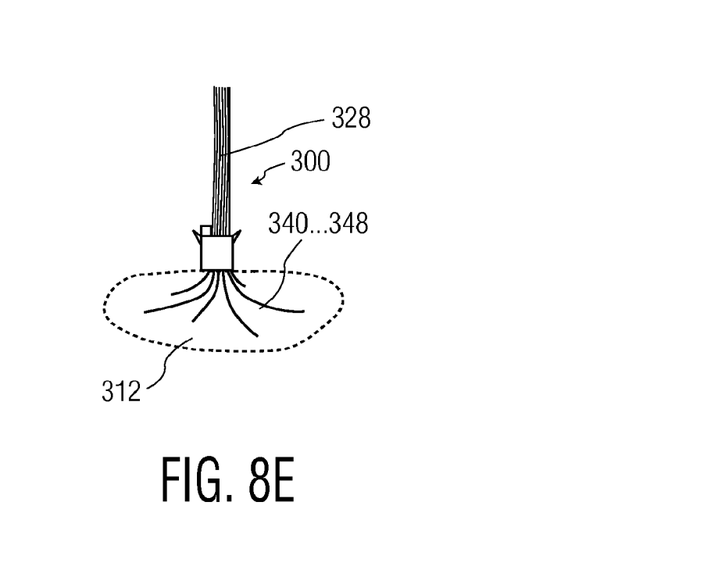

FIGS. 8A-E show, in sequence, illustrative steps of an implantation procedure using device 300 using implantation apparatus 600. In FIG. 8A, implantation apparatus 600, containing device 300, is disposed adjacent a targeted area 312 of the brain. Upon the downward movement of inner tube 604, leads 340 . . . 348 are displaced from within inner tube 602 and into targeted area, as shown in FIG. 8B. In FIG. 8C, leads 340 . . . 348 are fully extended into targeted area 312. As explained above, leads 340 . . . 348 may be prearranged (e.g., by length, number, relative position) such that, once fully extended, their distribution approximates the volume of targeted area 312. In FIG. 8D, inner tube 604 is partially withdrawn from outer tube 604. As noted above, lead wires 328 extend through inner tube 604, such that withdrawal of inner tube 604 leaves lead wires 328 and the rest of device 300 undisturbed. Finally, in FIG. 8E, both inner tube 604 and outer tube 602 have been fully withdrawn, leaving device 300 behind with leads 340 . . . 348 distributed within targeted area 312. If barbs 350, 352 are operable to extend outward after placement of device 300, they may be adapted to do so, for example upon the withdrawal of outer tube 602 from device 300, for example.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method for delivering an electrical stimulus to an individual, the method comprising administering the electrical stimulus to a tissue of the individual via an implantable medical device, the implantable medical device comprising:
    an assembly block; and
    a plurality of leads extending from the assembly block, wherein each of the plurality of leads includes at least one electrode, wherein the plurality of leads are configured such that the at least one electrode of each of the plurality of leads are distributed within a three-dimensional tissue space, wherein the assembly block and the plurality of leads are contained within a biodegradable encapsulant during implantation of the implantable medical device such that the at least one electrode of each of the plurality of leads assume a first distribution within the biodegradable encapsulant, and wherein the at least one electrode of each of the plurality of leads are configured to assume a second distribution upon degradation of the biodegradable encapsulant.

2. The method of claim 1, wherein the assembly block includes at least one barb for anchoring the assembly block within the tissue.

3. The method of claim 2, wherein the at least one barb is configured to be retracted toward the assembly block in a first position and extend from the assembly block in a second position.

4. The method of claim 1, wherein at least one of the plurality of leads includes more than one electrode.

5. The method of claim 1, wherein the biodegradable encapsulant is configured to protect the implantable medical device during implantation.

6. The method of claim 5, wherein the encapsulant includes at least one of the following: polylactic acid (PLA), polyglycolic acid (PGA), polydioxanone (PDS), polyethylene glycol (PEG), and polyhydroxy butyrate (PHB).

7. The method of claim 1, wherein the plurality of leads are prearranged such that the distribution of the electrodes corresponds to targeted volume of the tissue.

8. The method of claim 1, wherein administering includes administering the electrical stimulus to a volume of the tissue smaller than a maximum volume possible by using fewer electrodes than are contained within the plurality of leads.

9. The method of claim 1, further comprising
    recording neural activity within the three-dimensional tissue space using at least one of the electrodes.

10. The method of claim 1, wherein the electrical stimulus is configured to reduce a tremor suffered by the individual.

11. The method of claim 10, further comprising
    administering to the individual at least one anti-tremor medication.

12. The method of claim 1, wherein the individual is suffering from at least one of the following: Parkinson's Disease, depression, a bipolar disorder, an obsessive convulsive disorder and epilepsy.

13. The method of claim 1, further comprising implanting an implantable medical device in the patient.

14. The method claim 1, wherein the encapsulant includes an anti-inflammatory compound configured to be released while the encapsulant degrades.

* * * * *